United States Patent [19]
Nottke

[11] Patent Number: 4,924,878
[45] Date of Patent: May 15, 1990

[54] ACTUATING MECHANISM FOR BIOPSY NEEDLE

[76] Inventor: James E. Nottke, 8609 Piper La., Largo, Fla. 34647

[21] Appl. No.: 268,729

[22] Filed: Nov. 7, 1988

[51] Int. Cl.⁵ ............................................. A61B 10/00
[52] U.S. Cl. .................................... 128/751; 128/754
[58] Field of Search ........ 128/305, 310, 749, 751–755; 606/167, 170, 171

[56] References Cited

U.S. PATENT DOCUMENTS

| | | | |
|---|---|---|---|
| 4,256,119 | 3/1981 | Gauthier | 128/754 |
| 4,378,810 | 4/1983 | Ishizaki | 128/754 |
| 4,461,305 | 7/1984 | Cibley | 128/754 |
| 4,667,684 | 5/1987 | Leigh | 128/754 |
| 4,699,154 | 10/1987 | Lindgren | 128/754 |
| 4,733,671 | 3/1988 | Mehl | 128/754 |
| 4,735,215 | 4/1988 | Goto | 128/754 |

FOREIGN PATENT DOCUMENTS

WO83/03343  10/1983  World Int. Prop. O. .

Primary Examiner—Randall L. Green
Assistant Examiner—Randy Shay
Attorney, Agent, or Firm—Oltman and Flynn

[57] ABSTRACT

A spring-powered actuating device for operating the obturator and the cannula of a biopsy needle, and a cocking device removably attachable to the actuating device. The actuating device has a manually-operated trigger slide which controls separately the release of spring-powered slides for moving the obturator and the cannula so the surgeon determines the time interval between the release of the obturator and the later release of the cannula. The extent to which the trigger slide can be displaced manually is controlled by a manually adjustable safety slide which may be set in a first position to permit the trigger slide to release the slide for the obturator only and in a second position to permit the trigger slide to release the slide for the cannula. The cocking device, when attached to the actuating device, is movable pivotally toward the actuating device by squeezing them together manually and when so moved it retracts the slides for the obturator and the cannula to stress their springs which power them.

23 Claims, 3 Drawing Sheets

ACTUATING MECHANISM FOR BIOPSY NEEDLE

This invention relates to an actuating mechanism for a biopsy needle used to take a specimen of body tissue from a patient.

BACKGROUND OF THE INVENTION

A known type of biopsy needle has a needle-like obturator or stylet inside an outer sleeve, usually called a cannula, both extending from a hand-held housing and connected to separate operating handles. The free end of the obturator and the free end of the cannula are tapered for insertion into the body and the obturator has a tissue-receiving recess near its free end. The cannula covers the tissue-receiving recess in the obturator during their initial insertion into the body to a point close to where a tissue specimen is to be removed. Next, the obturator is pushed farther into the patient to extend the free end of the obturator from the cannula and expose the tissue-receiving recess to body tissue, which prolapses into this recess. Then, the cannula is pushed in so that it slides across the tissue-receiving recess in the obturator, severing the tissue specimen in that recess from the surrounding body tissue. Finally, the cannula and the obturator are withdrawn as a unit from the patient and the tissue specimen in the recess in the obturator is removed for analysis.

The biopsy needle is used in conjunction with an ultrasonic scanner having a display screen that shows the surgeon the position of the free ends of the obturator and the cannula in the patient's body.

One of the disadvantages of such biopsy needles is the relative slowness with which the obturator and the cannula can be safely operated manually after being inserted into the patient's body close to where the tissue specimen will be taken. When the tissue is relatively deep in the body and may have nerve endings, the slow sequential displacements of the obturator and the cannula can produce a substantial amount of perceived pain.

To overcome this problem, spring-operated biopsy needles have been used which, after insertion manually into the patient's body close to the desired location of the tissue specimen, produce relatively quick spring-powered movements, first, of the obturator, and then, of the cannula to capture a tissue specimen. These spring-operated biopsy needles have an automatic operation in which the tissue-severing movement of the cannula takes place immediately after the obturator is extended to receive body tissue in its recess, and the surgeon cannot change the brief time interval between exposure of the tissue-receiving recess in the obturator to the body tissue and the closing of that recess by the cannula to sever the tissue specimen in this recess. This time interval may be so brief that the specimen is damaged on the periphery because there was not sufficient time for the tissue to prolapse into the recess in the obturator before being severed by the cannula.

To offset this problem, one solution has been to lengthen this recess but this is unsatisfactory when sampling of a restricted area of the patient's body is desired. Also, it makes the captured tissue specimen too long to be ideally suited for pathology and the specimen is likely to have damaged cells near the ends.

Another disadvantage of such automatic, spring-operated biopsy needles is that they do not permit the surgeon to take a final view on the display screen of the ultrasonic scanner after the obturator has been extended to expose its specimen-receiving recess to the body tissue and before the cannula is extended to sever the tissue specimen and hold it in the recess in the obturator because the time interval between the two extensions is so brief.

SUMMARY OF THE INVENTION

This invention relates to a novel actuating mechanism for a biopsy needle which combines the advantages of spring-powered operation and separate manual control of the obturator and the cannula, enabling the surgeon to determine exactly when to sever the tissue specimen that has prolapsed into the recess in the obturator.

In addition to minimizing pain in the area of the patient's body where the tissue specimen is taken, the present invention permits the surgeon to determine the time interval between the extension of the obturator to expose its tissue-receiving recess and the closing of that recess and the severing of the tissue specimen by the extension of the cannula. Consequently, this time interval can be long enough to permit the body tissue to prolapse into this recess before the cannula severs it. This, in combination with the speed at which the spring-powered cannula moves when severing the tissue specimen, minimizes cell damage at the periphery of this captured specimen, particularly at its opposite ends lengthwise of the obturator and the cannula.

The present invention also enables the use of a biopsy needle whose specimen-receiving recess in the obturator has a length of about 1 cm. This provides a short tissue specimen that is easy to handle in pathology and has minimum contamination from damaged cells at the ends. This is possible because the surgeon can delay the tissue severing and capturing movement of the cannula until the tissue has had time to prolapse into the short recess in the extended obturator.

Another advantage of this invention is that after the obturator has been extended to receive a tissue specimen, if the surgeon determines that this specimen is not from the precise location desired, as shown on the display screen of the ultrasonic scanner, the surgeon may retract the obturator into the cannula and re-position them in the patient's body closer to the preferred location for taking a tissue specimen, and then he may extend the obturator again to receive a tissue specimen at this new location in the body, all before extending the cannula to capture a tissue specimen.

Another advantageous feature of the invention is that the springs which operate the obturator and the cannula are stressed by a cocking device that is readily separable from the actuating device so as not to interfere with its operation. The cocking device is operated manually by a squeezing operation in which it does not tend to introduce any inadvertent longitudinal motion of the obturator or the cannula. This minimizes the risk that the biopsy needle might enter an undesired area of the patient's body.

Also, the present invention has provision for selectively:

(1) preventing the release of either the obturator or the cannula, thus effectively "disarming" both of them; or (2) disarming the cannula only, even after the obturator has been released; or (3) permitting the release of both the obturator and the cannula, thus effectively "arming" both of them.

Another advantage of the actuating device of the present invention is that it can receive a biopsy needle of known design and proven reliability, converting that biopsy needle from its normal manual mode of operation to spring-powered operation but with no operational change in the biopsy needle itself.

Preferably, the actuating device of the present invention has a two-piece housing with a base and a back cover. The base has a front recess for receiving the housing of a biopsy needle of known design and a pair of slides on opposite sides of the recess for receiving the usual handles for the obturator and the cannula of the biopsy needle. The slides are powered by springs which can be compressed by a cocking device that is readily attachable to and separable from the housing of the actuating device. A push-button operated trigger slide inside the housing separately controls the release of the slides for the obturator and the cannula individually. A manually adjustable safety slide controls how the trigger slide can be operated.

Further objects and advantages of this invention will be apparent from the following detailed description of a presently preferred embodiment which is illustrated schematically in the accompanying drawings.

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

DETAILED DESCRIPTION

Figure 1:
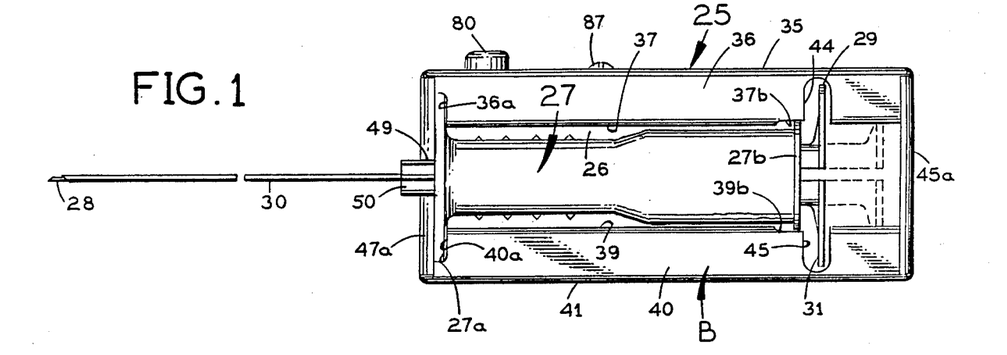
FIG. 1 is a front elevation of the present actuating device holding a biopsy needle of known design.

Referring to FIG. 1, the actuating device 25 of the present invention has a housing with a central longitudinal recess 26 in the front for receiving and holding the housing 27 of a biopsy needle of known design which is sold under the name "MONOJECT" by Sherwood Medical Company, St. Louis, Mo. This biopsy needle has an inner needle 28, obturator or stylet of solid cross-section connected to a finger button 29 and a hollow cylindrical sleeve or cannula 30 concentric with the obturator 28 and connected to a finger button 31. The obturator 28 and the cannula 30 are slidable about 1.3 cm. with respect to one another.

Figure 6:
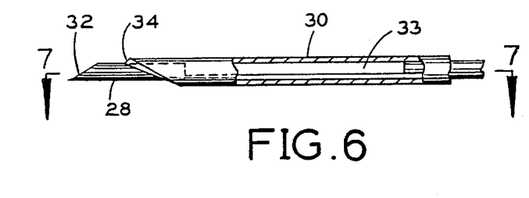
FIG. 6 is an enlarged view of the free end of the biopsy needle, partly in elevation and partly in section, with the obturator in its retracted position in the cannula.
Figure 7:
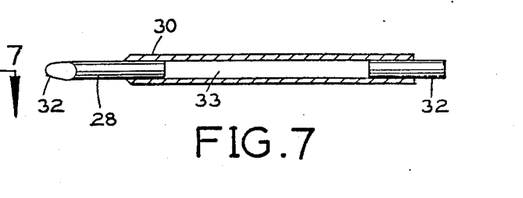
FIG. 7 is a longitudinal section taken along the line 7—7 in FIG.6.
Figures 18, 19:
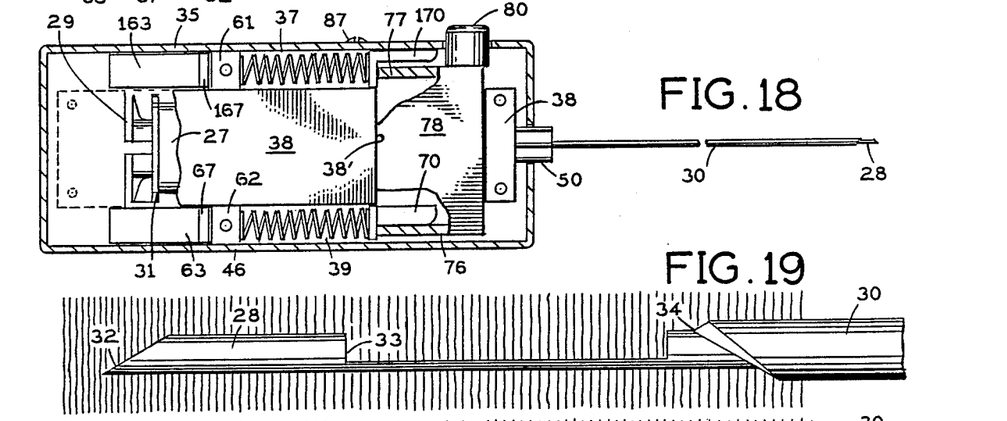
FIG. 18 is a similar view with the trigger slide in its fully pushed-in position.
FIG. 19 is a view showing the free end of the biopsy needle inserted into a patient and with the obturator extended from the cannula to expose its tissue-receiving recess.

Referring to FIG. 19, the obturator 28 has a tapered distal end tip 32 and a tissue-receiving recess 33 located a short distance behind this tip. Preferably, this recess is substantially 1 cm. long. The cannula 30 has a tapered distal end tip 34 which is just behind the recess 33 in the obturator 28 when the obturator is extended longitudinally from the cannula, as shown in this Figure. Normally, as shown in FIG. 6 and 7, the obturator 28 is retracted into the cannula 30 and the cannula completely covers the recess 33 in the obturator, with the tip of the obturator projecting slightly beyond the cannula.

Inside the housing 27 the "MONOJECT" biopsy needle has a mechanical interlock (not shown) which functions as follows:

Starting with both finger buttons 29 and 31 retracted as far as possible from housing 27, if finger button 29 is moved toward housing 27 it produces a like movement of the obturator 28 but no corresponding movement of the other finger button 31 or cannula 30, so that the free end of the obturator now projects about 1.3 cm. farther beyond the free end of the cannula. If now the other finger button 31 is pushed toward housing 27 it produces a corresponding movement of cannula 30 but no movement of obturator 28.

After moving the obturator's finger button 29 toward housing 27 but before moving the cannula's finger button 31 toward the housing, the finger button 29 may be retracted to pull the obturator 28 back into the cannula 30 without affecting the position of finger button 31 or the cannula.

Also, starting with both finger buttons 29 and 31 fully retracted from housing 27, if finger button 31 is moved toward the housing it causes the other finger button 29 and both the cannula 30 and the obturator 28 to move simultaneously in that direction.

Starting with both finger buttons 29 or 31 as close as possible to housing 27, if either of them is retracted away from the housing the other finger button is retracted simultaneously, as are the obturator 28 and the cannula 30.

Figure 20:
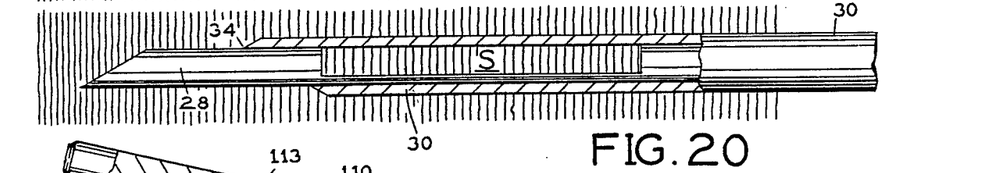
FIG. 20 is a similar view showing the cannula extended to sever the tissue sample and hold it in the recess in the obturator.

When this biopsy needle unit is operated manually by a surgeon, it is inserted into the patient with its obturator 28 in the retracted position shown in FIGS. 6 and 7 so that its tissue-receiving recess 33 is covered by the cannula 30. After reaching a location about 1 cm. from where a tissue specimen is to be taken from the patient's body, the obturator 28 is pushed to an extended position shown in FIG. 19, exposing its recess 33 to a small sample of the patient's tissue. This is done by manually moving the obturator's finger button 29 in that direction. Following this, the cannula 30 is pushed in the same direction to the position shown in FIG. 20, thereby severing the tissue specimen S that is in the obturator recess 33 from the surrounding tissue and trapping this severed tissue specimen in the obturator recess. This is done manually by moving the cannula's finger button 31 in that direction. Then both the obturator and the cannula are retracted simultaneously from the patient while continuing to maintain this same position of the cannula and obturator with respect to each other, thereby removing the severed tissue specimen S from the patient's body.

The actuating device 25 of the present invention has a housing (FIGS. 8-10) made up of a base B and a back cover C.

The base B has a flat top wall 35, a flat upper front wall 36 extending perpendicularly down from its top wall 35, a flat upper inner wall 37 extending perpendicularly rearward from the lower edge of the upper front wall 36 parallel to top wall 35, a generally flat bridging wall 38 extending perpendicularly down from the rear edge of the upper inner wall 37, a flat lower inner wall 39 extending perpendicularly forward from the lower edge of the bridging wall 38, a flat lower front wall 40 extending perpendicularly down from the front edge of the lower inner wall 39, and a flat bottom wall 41 extending perpendicularly rearward from the lower edge of the lower front wall 40. The inner walls 37 and 39 and bridging wall 38 together define the previously-mentioned central longitudinal recess 26 which receives the housing 27 of the biopsy needle. The top wall 35, upper front wall 36 and upper inner wall 37 together define a first longitudinal channel or guideway 42 of rectangular cross-section in the actuating device 25. The bottom wall 41, lower front wall 40 and lower inner wall 39 together define a second longitudinal channel or guideway 43 of rectangular cross-section in the actuating device. Both channels 42 and 43 extend along the complete length of the base. The bridging wall 38 is formed with a shallow rectangular recess 38' (FIGS. 5, 8 and 12) which is open at the back side of the base. Recess 38' at its opposite ends opens into the longitudinal channels or guideways 42 and 43 near the end of the base through which the cannula 30 and the obturator 28 project from the housing 27 of the biopsy needle.

Toward the opposite end of the actuating device 25 (the right end in FIG. 1), the upper front wall 36 of its base B is formed with a slot 44 extending up to its top wall 35. At this slot and to the right of it in FIG. 1, the upper inner wall 37 of the base is not present so that here the central longitudinal recess 26 opens into the upper channel or guideway 42.

Similarly, the lower front wall 40 of the base has a slot 45 located directly opposite the slot 44 in the upper front wall 36 and extending down to the bottom wall 41. At slot 45 and to the right of it in FIG. 1, the lower inner wall 39 is not present in the base so that here the central longitudinal recess 26 in the base opens into its lower channel or guideway 43.

The finger button 29 for the obturator 28 of the biopsy needle passes through the upper front slot 44 and the finger button 31 for the cannula 30 passes through the lower front slot 45 when the biopsy needle is put into the present actuating device 25. As shown in phantom in FIG. 1, each finger button 29 and 31 can be retracted to the right of the corresponding slot 44 or 45 along the respective channel or guideway 42 or 43 in the base B of the actuating device.

Figures 3, 4, 5:
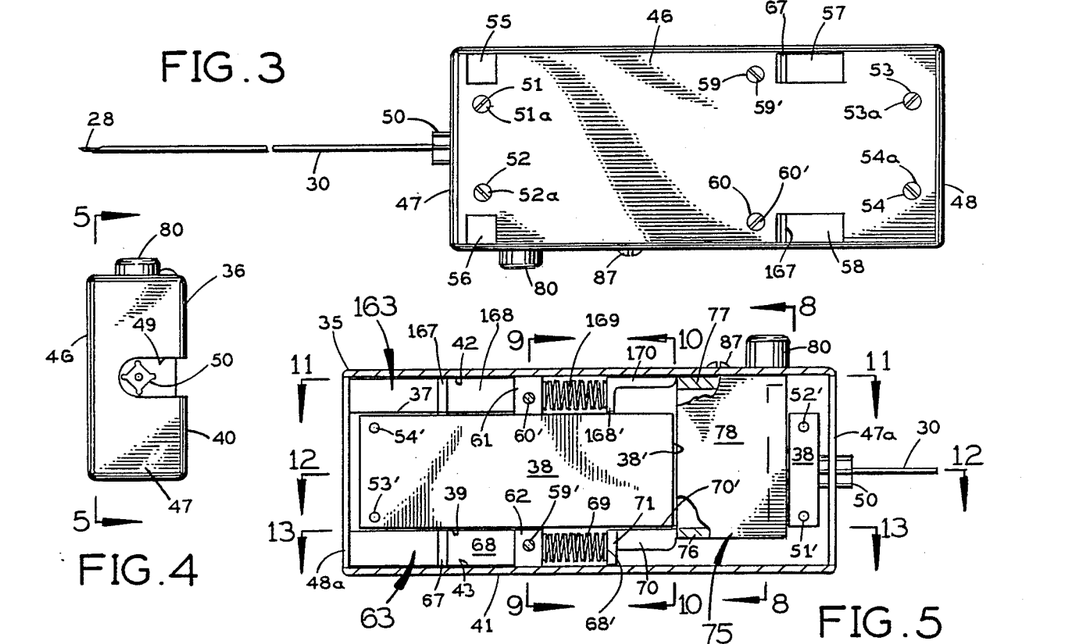
FIG. 3 is a rear elevation.
FIG. 4 is an end elevation taken from the left end of the actuating device in FIG. 1.
FIG. 5 is a longitudinal section taken along the line 5—5 in FIG. 4 at the inside of the back cover of the actuating device but showing the operating parts of the actuating device in a different condition than in FIGS. 1-4.
Figure 11:
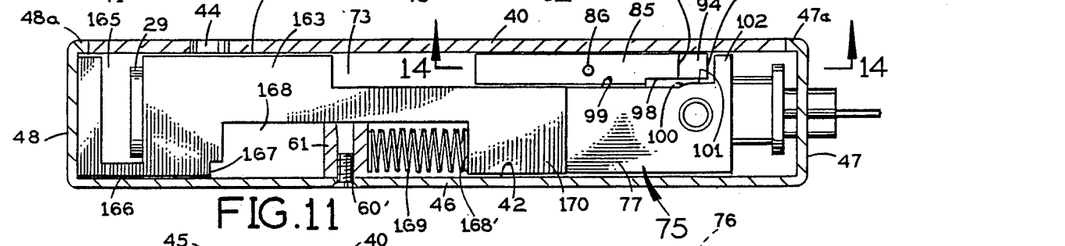
FIG. 11 is a longitudinal section taken along the line 11—11 in FIG. 5.

The back and the opposite ends of base B are closed by a one-piece cover C. As shown in FIGS. 3 and 11, the cover has a flat back wall 46 and end walls 47 and 48 extending perpendicular to it at opposite ends. End wall 47 is at the end of the actuating device where the cannula 30 and the obturator 28 of the biopsy needle project out. The end walls 47 and 48 of the cover are joined to respective inturned lips 47a and 48a (FIG. 11) which abut against the front walls 36 and 40 of the base at their opposite ends. The end wall 47 of the cover has a slot 49 (FIGS. 4 and 12) for snugly receiving the front nose 50 of the housing 27 of the biopsy needle.

Figure 8:
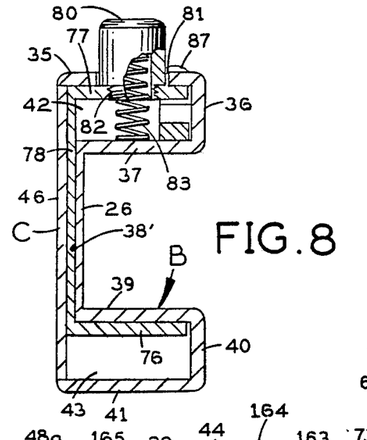
FIG. 8 is a cross-section taken along the line 8—8 in FIG. 5.
Figures 9, 10:
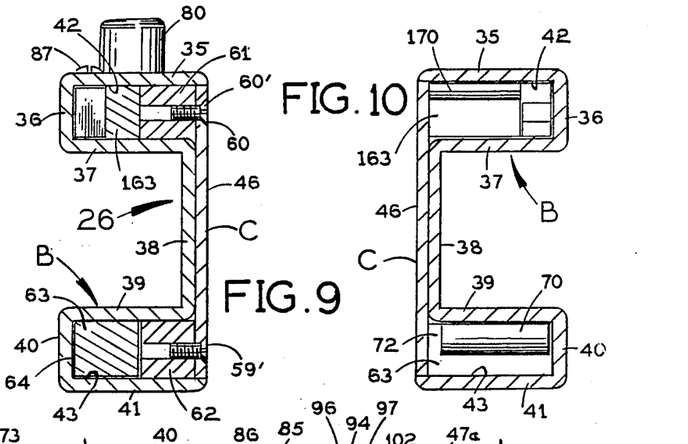
FIG. 9 is a cross-section taken along the line 9—9 in FIG. 5.
FIG. 10 is a cross-section taken along the line 10—10 in FIG. 5.
Figure 12:
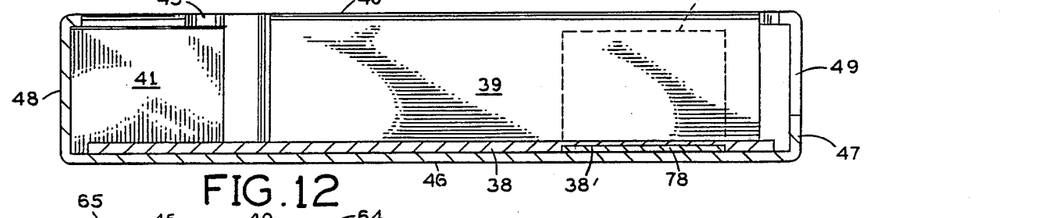
FIG. 12 is a longitudinal section taken along the line 12—12 in FIG. 5.

As shown in FIG. 3, the back wall 46 of the cover has a pair of circular openings 51 and 52 near its end wall 47 and a similar pair of openings 53 and 54 near its end wall 48. These openings register with the corresponding screw-threaded openings 51', 52', 53' and 54' (FIG. 5) in the bridging wall 38 of base B and they receive corresponding screws 51a, 52a, 53a and 54a (FIG. 3) for removably attaching cover C to base B. When the cover is attached to the base, the back wall 46 lies next to the bridging wall 38 of the base, as shown in FIG. 9, 10 and 12. As shown in FIGS. 8 and 12, the back wall 46 of cover C covers the open side of the shallow rectangular recess 38' in the base.

Referring to FIG. 1, the upper and lower front walls 36 and 40 and the adjoining inner walls 37 and 39 of base B are cut away at 36a and 40a on opposite sides of its central longitudinal recess 26 at the ends of the base where the cover's end wall 47 is located. The housing 27 of the biopsy needle has a transversely outwardly protruding end flange 27a which fits slidably between this cut-away end of the base and the cover's end wall 47. Flange 27a has a limited amount of "play" longitudinally of the actuating device once it is inserted past the inturned front lip 47a of end wall 47.

The upper and lower inner walls 37 and 38 of base B are recessed at 37b and 39b next to the slots 44 and 45 in the adjoining upper and lower front walls 36 and 40, making the central longitudinal recess 26 in the base slightly wider here. The housing 27 of the biopsy needle has a transversely outwardly protruding end flange 27b which fits slidably between walls 37 and 39 only at the recessed areas 37b and 39b.

The housing 27 of the biopsy needle can be inserted into the base B only when the finger buttons 29 and 31 for the obturator 28 and the cannula 30 are close to the end flange 27b of this housing, as shown in full lines FIG. 1. This positions the obturator 28 retracted into the cannula 30, with the specimen-receiving recess 33 in the obturator completely covered by the cannula and only the pointed end tip of the obturator projecting beyond the cannula. In this position of the parts of the biopsy needle, the end flange 27b of its housing can slide down into the longitudinal recess 26 in the base at the recessed areas 37b and 39b of its upper and lower inner walls 37 and 39, and the opposite end flange 27a of the biopsy needle housing 27 can slide down behind the end wall 47 of cover C at the cut-away areas 36a and 40a on this end of the base.

The back wall 46 of cover C has two rectangular openings 55 and 56 (FIG. 3) located outside its openings 51 and 52 near its end wall 47. The back wall 46 has two additional rectangular openings 57 and 58 which are located toward the opposite end wall 48 of the cover. Openings 57 and 58 are elongated lengthwise of the cover. Openings 56 and 58 in the cover open into the longitudinal channel 42 in the base. Openings 55 and 57 in the cover open into the longitudinal channel 43 in the base.

Figures 13, 14, 15, 16:
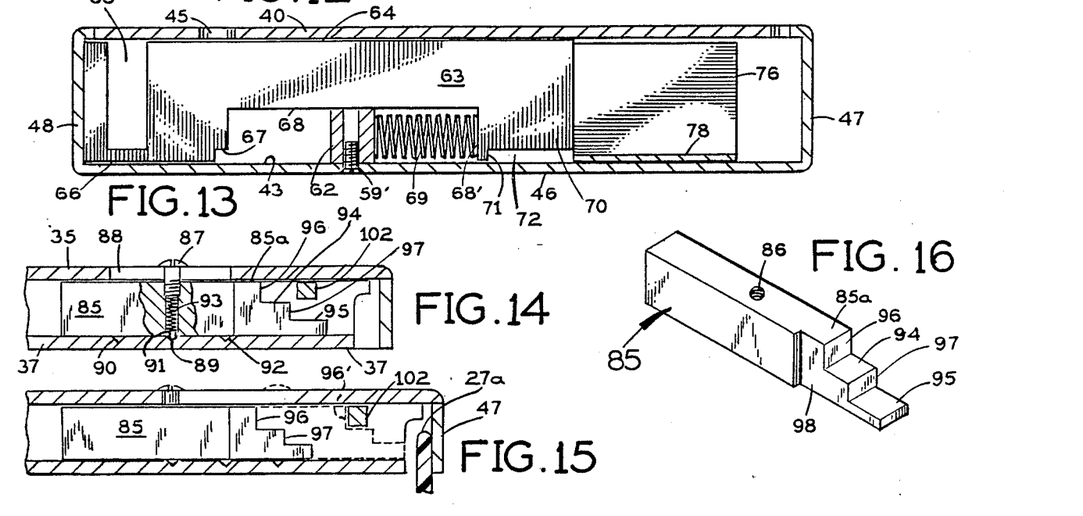
FIG. 13 is a longitudinal section taken along the line 13—13 in FIG. 5.
FIG. 14 is a longitudinal section taken along the line 14—14 in FIG. 11 with the safety slide in its middle position.
FIG. 15 is a similar view showing the safety slide in its fully-retracted position in full lines and in its fully-extended position in phantom.
FIG. 16 is a perspective view of the safety slide.

The back wall 46 of cover C has a third pair of circular openings 59 and 60 located close to its elongated rectangular openings 57 and 58, respectively, and receiving respective screws 59' and 60'. As shown in FIG. 5, screw 60' is screw-threadedly received in a rectangular stop block 61 that is snugly received in the longitudinal channel 42 in base B, and screw 59' similarly engages a rectangular stop block 62 snugly received in the other longitudinal channel 43 in the base. FIGS. 9, 11 and 13 show this in enlarged detail.

Referring to FIG. 13, a slide 63 for the cannula 30 of the biopsy needle unit is slidably received in channel or guideway 43 in the base. This slide has a flat longitudinal front face 64 which extends just inside the lower front wall 40 of the base and is interrupted by a deep rectangular recess 65 near the end of this slide adjacent the end wall 48 of cover C. This recess receives the finger button 31 for the cannula 30 of the biopsy needle with a certain amount of "play" between them longitudinally of the actuating device 25. Behind this recess 65 and on opposite sides of it in FIG. 13, slide 63 presents a flat longitudinal back face 66 which extends just inside the back wall 46 of cover C. In the direction toward the end of the actuating device where the biopsy needle projects out, this back face 66 of slide 63 ends at a relatively shallow rectangular notch 67, which has a short length longitudinally of the slide. A deeper and longer rectangular recess 68 extends from notch 67 to the right in FIG. 13. The previous-mentioned stop block 62 is received in recess 68. Recess 68 ends at a transverse end face 68' at its end away from notch 67.

A coil spring 69 is engaged under compression between the fixedly positioned stop block 62 and the end face 68' of recess 68 to bias slide 63 to the right in FIG. 13, i.e., toward the end of the actuating device where the biopsy needle projects out.

A short distance past the long recess 68, the slide 63 is reduced in cross-section, presenting a reduced end segment 70 (FIG. 5) extending beyond a flat transverse shoulder 71. End segment 70 is about half the thickness of the rest of the slide between the lower inner wall 39 and the bottom wall 41 of the base. As shown in FIG. 13, at this reduced end segment 70 the slide 63 presents a shallow longitudinal recess 72 along its back face adjacent the back wall 46 of cover C.

Referring to FIG. 11, a slide 163 for the obturator 28 of the biopsy needle is slidably received in the other longitudinal channel or guideway 42 in the base. Slide 163 is identical to the just-described slide 63 in most respects, and the detailed description of these features will not be repeated. Elements of slide 163 which correspond to elements of slide 63 are given the same reference numerals plus 100.

Slide 163 differs from slide 63 in the following particulars:

(1) slide 163 has a long rectangular recess 73 along its front side;

(2) its reduced end segment 170 does not have a longitudinal recess like the recess 72 in slide 63; and (3) its reduced end segment 170 has a thickness substantially less than half the thickness of the rest of slide 163 between the top wall 35 and the lower inner wall 37 of the base, as shown in FIG. 5.

A coil spring 169 is engaged under compression in channel 42 between the fixedly positioned stop block 61 and a transverse face 168' at one end of recess 168 in slide 163, so this spring biases slide 163 to the right in FIGS. 5 and 11.

Figure 17:
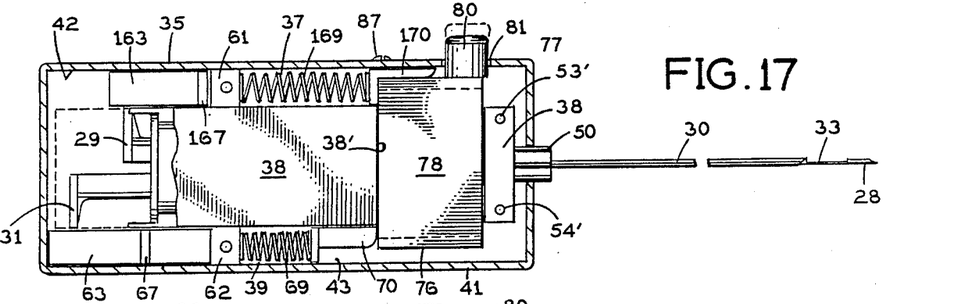
FIG. 17 is a longitudinal section showing the position of the parts when the trigger slide is in its intermediate position.

The present actuating device 25 has a trigger slide 75 (FIGS. 5 and 8) of generally channel-shaped cross-section, including a flat lower leg 76, a flat upper leg 77 extending parallel to lower leg 76, and a thinner flat back wall 78 extending perpendicular to the lower and upper legs. The lower leg 76 of the trigger slide is received in the longitudinal channel 43 of the base B, the upper leg 77 of the trigger slide is received in the other longitudinal channel 42, and the bridging wall 78 of the trigger slide is slidably received in the shallow recess 38' at the back of the bridging wall 38 of base B. The trigger slide 75 is slidably adjustable in base B transversely of its longitudinal channels 42 and 43 between:

(1) an upper position (FIG. 5) in which its upper leg 77 is next to the top wall 35 of the base and its lower leg 76 is next to the lower inner wall 39 of the base; and (2) an intermediate position (FIG. 17) in which its upper leg 77 is about midway between the top wall 35 and the upper inner wall 37 of the base and its lower leg 76 is about midway between the lower inner wall 39 and the bottom wall 41 of the base; and (3) a lower position (FIG. 18) in which its upper leg 77 is next to the upper inner wall 37 of the base and its lower leg 76 is next to the bottom wall 41 of the base.

In position (1) of the trigger slide (FIG. 5), its upper leg 77 blocks the reduced end segment 170 of the upper slide 163 and its bottom leg 76 blocks the reduced end segment 70 of lower slide 63. In position (2) of the trigger slide (FIG. 17), its lower leg 76 blocks the reduced end segment 70 of lower slide 63 and its upper leg 77 does not block the reduced end segment 170 of upper slide 163. In position (3), shown in FIG. 18, the upper leg 77 of the trigger slide does not block the reduced end segment 170 of the upper slide 163 and its bottom leg 76 does not block the reduced end segment 70 of lower slide 63.

As shown in FIG. 13, the lower leg 76 of the trigger slide 75 is rectangular and extends from the back wall 78 of the trigger slide almost to the lower front wall 40 of base B. However, as shown in FIG. 11, for most of its length the upper leg 77 of the trigger slide does not extend into close proximity to the lower front wall 40 of the base but instead presents a straight front edge 99 which extends parallel to wall 40 and is spaced from it by substantially the same distance as the bottom of the adjacent longitudinal recess 73 in the upper slide 163. Toward its right end in FIG. 11 this upper leg 77 of the trigger slide presents a convex corner at 100 and a straight longitudinal edge 101 extending from that corner and positioned slightly closer to wall 40 than its edge 99. At its right end in this Figure, the upper leg 77 of the trigger slide presents an extension 102 that extends almost to the lower front wall 40 of base B.

A trigger button 80 is attached to the upper leg 77 of the trigger slide 75 and extends loosely through an opening 81 in the top wall 35 of the base. As shown in FIG. 8, the trigger button has a reduced, screw-threaded stem 82 on its inner end which is threadedly received in a screw-threaded hole in the upper leg 77 of the trigger slide. The trigger button 80 has a hollow interior which receives a coil spring 83. Spring 83 is under compression between the trigger button and the upper inner wall 37 of base B. Spring 83 biases the trigger button 80 and the trigger slide 75 upward to the position shown in FIG. 8.

Figure 2:
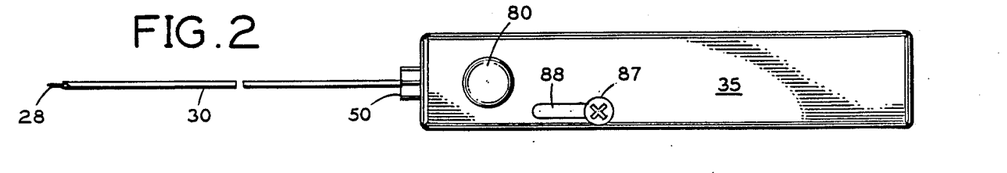
FIG. 2 is a top plan view.

The present actuating device has a safety slide 85 (FIGS. 11 and 16) which determines how far down the trigger button 80 can be pushed in from its spring-biased, upper position shown in FIG. 8. As shown in FIG. 11, the safety slide 85 is positioned between the front edge 99 of trigger slide 75 and the front wall 40 of base B and in the recess 73 in the slide 163 for the obturator 28 of the biopsy needle. As shown in FIG. 16, the safety slide has a screw-threaded recess 86 at the top. A bolt 87 (FIG. 2) extends loosely through an elongated slot 88 in the top wall 35 of the base and is threadedly received in recess 86 in safety slide 85. As shown in FIG. 14, on the bottom the safety slide has a spring-biased detent 89 with a rounded bottom face that is engageable selectively in any of three complementary shallow recesses 90, 91 and 92, which are spaced apart longitudinally of channel 42 on the inside face of the lower inner wall 37 of base B. A coil spring 93 in the safety slide 85 is engaged under compression between the inner end of bolt 87 and detent 89. FIG. 14 shows the bolt 87 positioned so that spring 93 holds the detent 89 in recess 91. Bolt 87 may be shifted longitudinally until the detent 89 snaps into one of the other recesses 90 or 92 to hold the safety slide 85 in a corresponding position.

Near its right end in FIG. 16 the safety slide 85 has a stepped construction, with a flat face 94 being its upper "step" and a flat face 95 being its lower "step". Faces 94 and 95 are parallel to the top face 85a of the safety slide. The safety slide presents a transverse, flat, end face 96 extending perpendicularly between its faces 85a and 94, and a transverse, flat, end face 97 extending between its faces 94 and 95.

At this stepped end the safety slide is formed with a shallow rectangular recess 98 on its back side. As shown in FIG. 11, this recess permits the safety slide 85 to be shifted to the right with respect to the trigger slide 75 until the transverse end face 96 of the safety slide is next to the extension 102 of the trigger slide, as shown in phantom in FIG. 15. This is the position of the safety slide in which its spring-pressed detent 89 is in recess 92 in the upper inner wall 37 of base B. In this position, the upper "step" 94 of the safety slide is just below the extension 102 of trigger slide 75 and the trigger button 80 cannot be pushed in. Also, in this position the stepped end of safety slide 85 holds the end flange 27a of the biopsy needle housing 27 against the end wall 47 of cover C to prevent accidental removal of the biopsy needle housing from the present actuating device.

FIGS. 11 and 14 show the safety slide 85 in its middle position, with its spring-biased detent 89 seated in the middle recess 91 along the upper inner wall 37 of the base. In this position of the safety slide its lower "step" 95 is in the path of the trigger slide extension 102 when the trigger button 80 is pushed down in. Therefore, the trigger slide 75 can move in only as far as its middle position (FIG. 17) when the trigger button is pushed in with the safety slide 85 in its middle position.

As shown in full lines in FIG. 15, when the safety slide 85 is positioned with its spring-biased detent 89 seated in the recess 90, the safety slide is completely retracted with respect to the trigger slide extension 102 and, when the trigger button 80 is pushed in, the trigger slide 75 can move to the position shown in FIG. 18.

Figure 21:
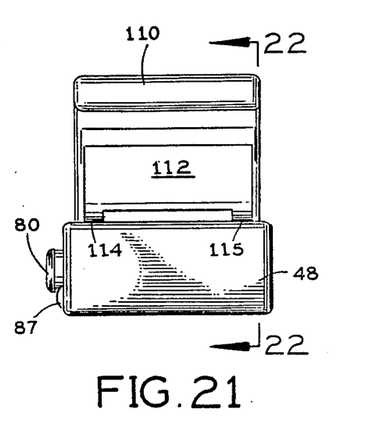
FIG. 21 is an end elevation taken from the right end of the actuating device in FIG. 2 and with the cocking device in place.
Figure 22:
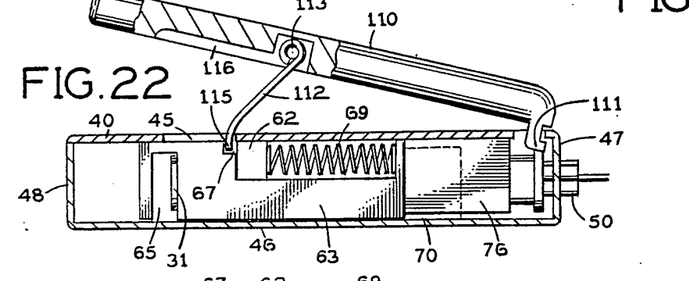
FIG. 22 is a longitudinal section taken along the line 22—22 in FIG. 21 and showing the cocking device before it retracts the needle slides in the actuating device.
Figure 23:
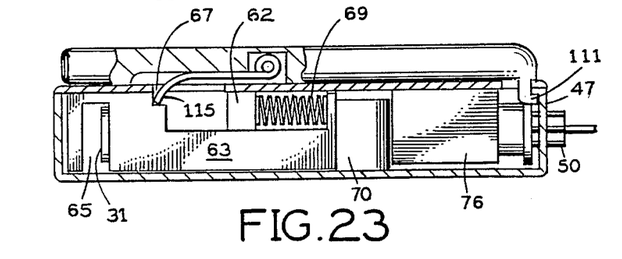
FIG. 23 is a similar view showing the position of the parts after the cocking device has retracted the needle slides.

Starting with the trigger slide in its fully pushed-in position (FIG. 18), the actuating device can be cocked (i.e., its springs 69 and 169 compressed to the fullest extent possible) by the cocking device shown in FIGS. 21–23.

This cocking device has a substantially flat plate 110 with two downwardly projecting, generally L-shaped ears 111 at one end. These ears can be inserted into the openings 55 and 56 (FIG. 3) in the cover C of the actuating device to mount the cocking device pivotally on the actuating device 25. A generally flat hinge plate 112 is pivotally mounted at one end on a fixed cross pin 113 in plate 110. At the opposite end, the hinge plate presents a pair of curved tangs 114 and 115 which are insertable into the openings 57 and 58 (FIG. 3) in the bottom wall 46 of cover C. As shown in FIG. 22, the hinge plate tang 115 is received in the notch 67 in slide 63 directly behind the fixed stop block 62 when spring 69 biases this slide to the right in FIG. 22. Similarly, the other hinge plate tang 114 is received in the notch 167 in slide 163 directly behind the stop block 61, with spring 169 biasing the slide 163 in the same direction as slide 63 is biased by its spring 69.

When the cocking plate 110 is brought to the position shown in FIG. 23, which is done by manually squeezing the actuating device 25 and the cocking plate 110 together, the pivoted hinge plate 112 pushes the slides 63 and 163 to the left in FIGS. 22 and 23, thereby compressing the springs 69 and 169 more. The cocking plate 110 has a shallow recess 116 which receives the flat part of hinge plate 112 when this action takes place.

Both slides 63 and 163 are retracted completely behind the trigger slide 75 and its bias spring 83 pushes the trigger slide to the position shown in FIG. 5, in which it now blocks both slides from moving to the right. Both slide springs 69 and 169 now are fully compressed.

Initially, the biopsy needle housing 27 is inserted into the present actuating device as shown in FIG. 1, with the nose 50 of the biopsy needle housing received in slot 49 in the end wall 47 of cover C, and the obturator 28 retracted with respect to the cannula 30. The end flange 27a of the biopsy needle housing 27 fits snugly between the end plate 47 of cover C and the adjacent cut-away end of base B (at 36a and 40a), the opposite end flange 27b of the biopsy needle housing 27 fits between the reduced areas 37b and 39b of the upper and lower inner walls 37 and 39 of the base, the finger button 29 for the obturator 28 is received in slot 165 in the needle slide 163 in channel 42 of the base at slot 44 in the upper front wall 36 of the base, and the finger button 31 for the cannula 30 is received in slot 65 in the needle slide 63 in channel 43 of the base at slot 45 in the base. Both springs 37 and 39 for the needle slides are expanded, as shown in FIG. 18. The safety slide 85 is in the full-line position of FIG. 15 so as to permit the needle slides 63 and 163 to be retracted.

The biopsy needle is inserted into the patient until its distal end is close to where the tissue specimen is to be taken.

Then the cocking device 110–116 (FIGS. 21–23) is attached to the actuating device and is operated to cock both needle slides, retracting them from the original position (FIGS. 18 and 22) in which their springs 37 and 39 are expanded to the cocked position (FIGS. 5 and 23) in which both springs are fully compressed. Spring 83 (FIG. 8) now moves trigger button 80 out from the top wall 35 of base B and positions the trigger slide 75 as shown in FIG. 5, holding both needle slides 63 and 163 retracted.

Then the safety slide 85 is moved to the position shown in phantom in FIG. 15, in which it prevents the trigger slide 75 from being pushed in and it holds the end flange 27a of the biopsy needle housing 27 against the end wall 47 of cover C. Following this, the cocking device 110–116 is removed from the actuating device 25. The distal end of the biopsy needle now is positioned within the patient about 1 cm. from where the tissue specimen is to be removed.

Next, the safety slide 85 is retracted to its half-way position (FIG. 14) in which its spring-pressed detent 89 is seated in recess 91. When the trigger button 80 now is pushed in, the trigger slide 75 moves in until its extension 102 engages the end "step" 95 of safety slide 85. This is the position of the trigger slide shown in FIG. 17, from which it will be evident that the trigger slide has released the cocked slide 163 for the obturator 28 of the biopsy needle, which is moved by its spring 169 to the extended position shown in this Figure. Recess 33 in obturator 28 is exposed to the patient's body tissue, and the tissue specimen prolapses into this recess while the slide 63 for the cannula 30 is held retracted by trigger slide 75.

After a time determined by the surgeon as sufficient for the tissue specimen to fully prolapse into the obturator recess 33, and if the surgeon now determines from the display screen of the ultrasonic scanner that this is where he wants the specimen taken, the surgeon retracts the safety slide 85 to the full-line position of FIG. 15, in which its spring-pressed detent 89 is in the recess 90 farthest from trigger button 80. Then the surgeon pushes the trigger button 80 in as far as it will go, the trigger slide extension button 102 being free to move completely past the safety slide 85, so that the trigger slide 75 reaches the position shown in FIG. 18. This releases the cocked slide 63 for the cannula 30, which under the impetus of spring 39 moves out along the obturator 28 to sever the tissue specimen that is in the obturator recess 33 from the adjoining body tissue and holds the captured tissue specimen in this recess.

Alternatively, instead of moving the safety slide 85 to its half-way position (FIG. 14) and thereafter to its fully retracted position (FIG. 15, full lines), the safety slide 85 may be moved in one stroke from its fully disarmed position (in phantom in FIG. 15) to its fully armed position (full lines in FIG. 15). The surgeon can then move the trigger button 80 half-way in to release the obturator 28 and then all the way in to release the cannula 30 with the time interval between such movements controlled by the surgeon.

As another alternative, the surgeon can move the trigger button 80 all the way in using one stroke, producing rapid-fire sequential movements of the obturator 28 and then the cannula 30 where the time interval between them is determined by the speed at which the trigger slide 75 is pushed in. As already explained, in many surgical situations this would be less satisfactory because the surgeon does not control the time interval for the tissue specimen to prolapse into the obturator recess 33 before it is severed by the cannula 30.

The actuating device 25 may be removed from the housing 27 of the biopsy needle after the sequential extensions of the obturator 28 and the cannula 30, as described, while the obturator and the cannula remain in the patient's body. Then the biopsy needle may be pulled out of the patient's body and the captured tissue specimen may be removed from the biopsy needle.

The present actuating mechanism (i.e., the actuating device 25 and the cocking device 110–116) is particularly advantageous for use in biopsy situations which are concerned with cancerous tissue, about 75% of which is located within 1 cm. of the capsule surrounding an organ, such as the prostate gland. In such situations it is undesirable to fire the obturator and the cannula of the biopsy needle more than about 1 cm. The present invention makes it possible in such situations to take a tissue specimen ideally suited for pathology.

I claim:

1. An actuating device for use with a biopsy needle having:

a housing;

an elongated cannula extending from said housing and terminating in a distal end away from said housing;

and an obturator extending from said housing longitudinally through said cannula and terminating in a distal end away from said housing, said obturator having a specimen-receiving recess near its distal end which is open along the outside of the obturator;

said obturator and said cannula being slidable with respect to each other between (a) a position in which said cannula covers said recess in the obturator and (b) a position in which said recess in the obturator is exposed beyond said distal end of the cannula for receiving a tissue specimen;

said actuating device comprising:

a base having a recess for receiving said housing of the biopsy needle and first and second guideways outside said recess;

a first needle slide slidably received in said first guideway and connectable to said obturator to determine the position of said distal end of the obturator from said housing of the biopsy needle received in said recess;

first spring means acting on said first needle slide to move said distal end of the obturator away from said housing of the biopsy needle received in said recess;

a second needle slide slidably received in said second guideway and connectable to said cannula to determine the position of said distal end of the cannula from said housing of the biopsy needle received in said recess;

second spring means acting on said second needle slide to move said distal end of the cannula away from said housing of the biopsy needle received in said recess;

and manually operable means for selectively releasing said first and second needle slides separately for movement of said obturator to said position in which said specimen-receiving recess is exposed, followed by movement of said cannula to said position covering said recess in the obturator after a time interval determined by the manual operation of said manually operable means.

2. An actuating device according to claim 1 wherein:

said needle slides are movable to respective retracted positions along said guideways to stress said first and second spring means;

and said manually operable means is engageable with said needle slides in their respective retracted positions and is selectively movable to (a) a position releasing said first needle slide from its retracted position but preventing movement of said second needle slide from its retracted position and (b) a different position releasing said second needle slide from its retracted position.

3. An actuating device according to claim 2 wherein said manually operable means comprises a trigger slide movable transversely of said guideways between (a) a position holding both of said needle slides in their respective retracted positions, (b) a position releasing said first needle slide from its retracted position but holding said second needle slide in its retracted position, and (c) a position releasing said second needle slide from its retracted position as well as releasing said first needle slide from its retracted position.

4. An actuating device according to claim 3 and further comprising a safety device selectively adjustable manually between (a) a position retaining said trigger slide in said position holding both said needle slides retracted, and (b) a position enabling said trigger slide to be moved to said position releasing said first needle slide from its retracted position but holding said second needle slide in its retracted position, and (c) a position enabling said trigger slide to be moved to said position releasing both said needle slides from their respective retracted positions.

5. An actuating device as in claim 4 further comprising a cocking device detachably connected to said actuating device and manually operable, when said trigger slide is in said position releasing both said needle slides, to move said needle slides from their released positions to their retracted positions, thereby stressing said first and second spring means.

6. An actuating device as in claim 5 wherein said cocking device is connected to said actuating device for pivotal movement toward said actuating device by manually squeezing them together.

7. An actuating device as in claim 1 further comprising a cocking device detachably connected to said actuating device and manually operable to move said needle slides to their retracted positions, thereby stressing said first and second spring means;

said manually operable means being selectively engageable with said needle slides to hold them retracted.

8. An actuating device as in claim 7 wherein:

said cocking device comprises a plate-like member having a laterally spaced pair of offset ears at one end, and a hinge plate pivotally connected to said plate-like member away from said ears and terminating away from its pivotal connection to said plate-like member in a pair of laterally spaced tangs;

said actuating device has a first pair of openings therein for receiving said ears to permit pivotal movement of said plate-like member toward and away from said actuating device;

said actuating device has a second pair of openings therein positioned to receive said tangs when said ears are inserted into said first pair of openings, said second pair of openings being elongated lengthwise of said actuating device;

and said first and second needle slides have respective notches therein which are exposed at said second openings in the actuating device to receive said tangs of said hinge plate;

said plate-like member of the cocking device, when pivoted toward said actuating device, pivoting said hinge plate in a direction to move said first and second needle slides to their respective retracted positions.

9. An actuating mechanism for use with a biopsy needle having:

a housing;

an elongated cannula extending from said housing and terminating in a distal end away from said housing;

and an obturator extending from said housing longitudinally through said cannula and terminating in a distal end away from said housing, said obturator having a specimen-receiving recess near its distal end which is open along the outside of the obturator;

said obturator and said cannula being slidable with respect to each other between (a) a position in which said cannula covers said recess in the obturator and (b) a position in which said recess in the obturator is exposed beyond said distal end of the cannula for receiving a tissue specimen;

said actuating mechanism comprising:

an actuating device having movable spring-powered means for moving the distal ends of said obturator and said cannula away from said housing, and manually operable means for holding said obturator and said cannula against such movement by said spring-powered means, said manually operable means being operable to selectively release said obturator and said cannula individually for movement by said spring-powered means;

and a cocking device detachably connected to said actuating device and manually operable to move said spring-powered means to a position holding the distal ends of said obturator and said cannula toward said housing, said cocking device being connected to said actuating device for pivotal movement toward said actuating device by manually squeezing them together.

10. An actuating device for use with a biopsy needle having:

a housing;

an elongated cannula extending from said housing and terminating in a distal end away from said housing;

and an obturator extending from said housing longitudinally through said cannula and terminating in a distal end away from said housing, said obturator having a specimen-receiving recess near its distal end which is open along the outside of the obturator;

said obturator and said cannula being slidable with respect to each other between (a) a position in which said cannula covers said recess in the obturator and (b) a position in which said recess in the obturator is exposed beyond said distal end of the cannula for receiving a tissue specimen;

a first finger button coupled to said obturator and located outside said housing;

and a second finger button coupled to said cannula and located outside said housing;

said actuating device comprising:

a base having a recess for receiving said housing of the biopsy needle and first and second guideways outside said recess;

a first needle slide slidably received in said first guideway and having means for holding said first finger button of said biopsy needle whose housing is received in said recess;

first spring means acting on said first needle slide to move said distal end of the obturator of said biopsy needle away from said housing of the biopsy needle;

a second needle slide slidably received in said second guideway and having means for holding said second finger button of said biopsy needle;

second spring means acting on said second needle slide to move said distal end of the cannula of said biopsy needle away from said housing of the biopsy needle;

said first and second needle slides being movable to respective retracted positions along said guideways to stress said first and second spring means;

and a manually operable trigger slide selectively adjustable transversely of said guideways between (a) a position holding both said first and second needle slides in their respective retracted positions, and (b) a position releasing said first needle slide from its retracted position but holding said second needle slide in its retracted position, and (c) a position releasing said second needle slide from its retracted position as well as releasing said first needle slide.

11. An actuating device according to claim 10 further comprising a safety slide selectively adjustable manually between (a) a position retaining said trigger slide in said position holding both said needle slides retracted, and (b) a position enabling said trigger slide to be moved to said position releasing said first needle slide from its retracted position but holding said second needle slide in its retracted position, and (c) a position enabling said trigger slide to be moved to said position releasing both said needle slides from their respective retracted positions.

12. An actuating device as in claim 11 further comprising a cocking device detachably connected to said actuating device for pivotal movement toward said actuating device by squeezing them together manually, said cocking device having means for moving said first and second needle slides to their respective retracted positions in response to said pivotal movement of the cocking device toward the actuating device when said trigger slide is in said position releasing both said first and second needle slides.

13. An actuating device as in claim 11 wherein said safety slide includes means for engaging said housing of the biopsy needle unit to hold said housing in said recess in said base of said actuating device when said safety slide is in said position retaining said trigger slide in its position holding both said needle slides retracted.

14. An actuating device as in claim 13 and further comprising spring means biasing said trigger slide to said position holding both said needle slides in their respective retracted positions.

15. An actuating device as in claim 11 and further comprising spring means biasing said trigger slide to said position holding both said needle slides in their respective retracted positions.

16. An actuating device as in claim 10 further comprising a cocking device detachably connected to said actuating device for pivotal movement toward said actuating device by squeezing them together manually, said cocking device having means for moving said first and second needle slides to their respective retracted positions in response to said pivotal movement of the cocking device toward the actuating device when said trigger slide is in said position releasing both said first and second needle slides.

17. An actuating mechanism as in claim 16 wherein:

said cocking device comprises a plate-like member having a laterally spaced pair of offset ears at one end, and a hinge plate pivotally connected to said plate-like member away from said ears and terminating away from its pivotal connection to said plate-like member in a pair of laterally spaced tangs;

said actuating device has a first pair of openings therein for receiving said ears to permit pivotal movement of said plate-like member toward and away from said actuating device;

said actuating device has a second pair of openings therein positioned to received said tangs when said ears are inserted into said first pair of openings, said second pair of openings being elongated lengthwise of said actuating device;

and said first and second needle slides have respective notches therein which are exposed at said second openings in the actuating device to receive said tangs of said hinge plate;

said plate-like member of the cocking device, when pivoted toward said actuating device, pivoting said hinge plate in a direction to move said first and second needle slides to their respective retracted positions.

18. An actuating device as in claim 10 and further comprising spring means biasing said trigger slide to said position holding both said first and second needle slides in their respective retracted positions.

19. An actuating device according to claim 10 wherein:

said recess in the base extends longitudinally of the base and said first and second guideways are located on opposite sides of said recess;

said trigger slide is slidably mounted on said base for selective manual adjustment across said guideways in the base between first, second and third positions, said trigger slide having a first leg in said first guideway and a second leg in said second guideway;

said first needle slide has a reduced end segment which is engageable with said first leg of the trigger slide in said first position of the trigger slide and is slidable past said first leg in second and third positions of the trigger slide;

and said second needle slide has a reduced end segment which is engageable with said second leg of the trigger slide in said first and second positions of the trigger slide and is slidable past said second leg in said third position of the trigger slide.

20. An actuating device according claim 19 and further comprising a safety slide slidably received in one of said guideways in the base and having a stepped end segment for controlling the extent to which said trigger slide can be moved across said guideways, said safety slide being slidably adjustable between a first position holding said trigger slide in said first position thereof, and a second position permitting manual displacement of said trigger slide to said second position thereof, and a third position permitting manual displacement of said trigger slide to said third position thereof.

21. An actuating device according to claim 20 and further comprising:

a trigger button connected to said trigger slide and extending slidably through said base;

and a spring acting between said trigger button and said base and biasing said trigger button out from the base to position said trigger slide in said first position thereof.

22. An actuating device according to claim 21 wherein said base has slots therein extending outward from said recess into said first and second guideways, respectively, said slots being positioned to pass said first and second finger buttons of the biopsy needle into said guideways when said housing of the biopsy needle is inserted into said recess in the base;

and said first and second needle slides have respective recesses for holding said first and second finger buttons of the biopsy needle, said recesses in the needle slides registering with said slots in the base only when said first and second needle slides are in their respective released positions.

23. An actuating device according to claim 10 wherein said base has slots therein extending from said recess into said first and second guideways, respectively, said slots being positioned to pass said first and second finger buttons of the biopsy needle into said guideways when said housing of the biopsy needle is inserted into said recess in the base;

and said first and second needle slides have respective recesses for holding said first and second finger buttons of the biopsy needle, said recesses in the needle slides registering with said slots in the base only when said first and second needle slides are in their respective released positions.

* * * * *